United States Patent [19]

Ort

[11] 4,040,953
[45] Aug. 9, 1977

[54] ANAEROBIC DIGESTION PROCESS

[75] Inventor: Jay E. Ort, Lewistown, Pa.

[73] Assignee: RecTech, Inc., State College, Pa.

[21] Appl. No.: 665,606

[22] Filed: Mar. 10, 1976

[51] Int. Cl.$^2$ .............................................. C02C 1/14
[52] U.S. Cl. ..................................... 210/6; 48/197 A;
71/10; 195/33; 210/12; 210/16
[58] Field of Search .................... 48/197 A; 71/10–14;
195/33; 210/2–9, 11, 12, 16, 18

[56] References Cited
U.S. PATENT DOCUMENTS

| | | | |
|---|---|---|---|
| 1,420,250 | 6/1922 | Gavett | 210/2 |
| 2,029,702 | 2/1936 | Buswel | 210/2 |
| 2,429,589 | 10/1947 | Wiley | 195/33 |
| 2,881,137 | 4/1959 | Logan | 210/14 |
| 3,259,566 | 7/1966 | Torpey | 210/16 |
| 3,769,204 | 10/1973 | Kincannon et al. | 210/8 |
| 3,847,803 | 11/1974 | Fisk | 210/16 |
| 3,981,800 | 9/1976 | Ort | 210/16 |

OTHER PUBLICATIONS

Sen et al., "Anaerobic Digestion of Liquid Molasses Distillery Wastes," WPCFJ, Oct. 1962, pp. 1015–1025.

*Primary Examiner*—Wilbur L. Bascomb, Jr.
*Assistant Examiner*—Peter A. Hruskoci

[57] ABSTRACT

The present invention relates to the manufacture of high calorific fuel gas through a process of anaerobic digestion involving retention of a slurry of organic material, maintained at a predetermined volume-to-interface (V/I) ratio and for a desired liquid retention time, pH and temperature to produce substantial amounts of methane gas while minimizing the production of carbon dioxide gas. When operating in the preferred range of volume-to-interface (V/I) relationships, the faster molecular diffusion rate of methane from the slurry as compared with carbon dioxide gas allows virtually all of the methane to be collected from the slurry while a considerably smaller amount of carbon dioxide gas is collected. Instead, the bulk of the carbon dioxide remains in the spent slurry which is transferred as sludge to a loop for carbon dioxide stripping. Liquid retention is controlled by a recirculation-stripping loop. Stripping of the carbon dioxide from the sludge in this loop is greatly improved by adjustment of pH with acid.

7 Claims, 3 Drawing Figures

FLOWSHEET
OF THE
PREFERRED EMBODIMENT

FLOWSHEET OF THE PREFERRED EMBODIMENT

ANAEROBIC DIGESTION PROCESS

This invention relates to an organic conversion system and process thereof, and more particularly to means and process for obtaining a high calorific product gas comprised primarily of methane and with a minor amount of carbon dioxide. The residue produced by the process has potential value either as a soil conditioner or organic fertilizer or as a protein-rich animal feel supplement.

It is well known in the art that anaerobic processes have been used as a method of stabilization of municipal sewage sludge and as such the fermentation is primarily for the destruction of the waste matter, rather than the production of fuel gas or other by-products.

The production of methane by the anaerobic digestion of the organic fraction of the municipal solid waste is a technically feasible, economically viable process, which is immediately available to relieve our natural gas shortage.

It is known that when organic materials are allowed to decompose in an oxygen deficient environment, methane gas is generated. However, carbon dioxide is also generated and carbon dioxide is a contaminant since as naturally formed in a conventional anaerobic process, the carbon dioxide is present from 30% to 40% in weight of the total gaseous product. The presence of the carbon dioxide reduces the heating value to 600 BTU per cubic foot as compared to 1,000 BTU per cubic foot of natural gas.

Accordingly, the gaseous product of a conventional anaerobic process must be subjected to a costly scrubbing process.

It has been suggested in co-pending Ort U.S. Pat. application Ser. No. 526,176 now Pat. No. 3,981,800, to carry out the anaerobic digestion process under several atmospheres of pressure including a recirculation loop featuring pressure release and degassing of carbon dioxide with the degassed sludge then pumped under pressure back into a digestion tank. The recirculation rate in the process of Ort U.S. application Ser. No. 526,176 is designed to maintain sludge in the digester in an unsaturated state with regard to carbon dioxide solubility, thereby keeping the carbon dioxide from precipitating out of the sludge within the digestion tank. This results in high-purity methane production. In another system of Ort U.S. application Ser. No. 526,176, similar results are accomplished by periodically depressurizing the digestion tanks to allow carbon dioxide to escape.

It has also been proposed in U.S. Pat. No. 3,838,199 to obtain fuel gas from animal waste through anaerobic fermentation of the slurry, but the product of this process is a gas containing 52% methane and 46% carbon dioxide. Similarly in U.S. Pat. No. 1,420,250 has an absence of any step to retard or remove the naturally produced carbon dioxide.

In contradistinction to the known prior art, the present invention involves an anaerobic digestion process where formation of gaseous carbon dioxide is suppressed and greatly minimized without effect upon methane production and indeed to the benefit of methane production. Through the present invention there is a recognition that gaseous methane has a coefficient of diffusion which is 4.53 greater than that of gaseous carbon dioxide. Thus, by carrying anaerobic process at predetermined volume-to-interface (V/I) ratios, the transfer of carbon dioxide across the interface within the digestion tank is minimized while the transfer of methane gas is maximized. The transfer across the interface takes place for a desired liquid retention time (LRT), temperature and pH.

With the process of the present invention, the gaseous product can be greater than 90% methane instead of the normally produced 50% to 70% methane. At the same time the carbon dioxide gaseous content is lowered to 10% or less instead of the naturally produced 30% to 50%. The gaseous product of the anaerobic process of the present invention is therefore considerably upgraded to high calorific values which heretofore had been attained only through a commercially available, but expensive scrubbing acid process which in itself consumes 20% to 30% of the methane gas as a power requirement.

It is accordingly an object of the present invention to manufacture a high calorific fuel gas through a process of anaerobic digestion.

Another object of the present invention is to convert organic materials into a high calorific fuel gas by control of the volume-to-interface (V/I) ratio.

A further object of the invention is to convert organic materials into a high calorific fuel gas by control of the liquid retention time (LRT) temperature and pH.

Yet another object of the present invention is to carry out an anaerobic digestion process which takes advantage of the faster diffusion rate of methane gas as compared with carbon dioxide gas to obtain a substantially complete recovery of the methane gas with a minimum of the carbon dioxide gas.

A still further object of the invention is to maintain the bulk of the carbon dioxide in the spent slurry for transfer as sludge to a loop for carbon dioxide stripping.

Still another object of the present invention is to achieve a residue from an anaerobic digestion process, which residue has potential value either as a soil conditioner, and organic fertilizer or as a protein-rich animal feed supplement.

The foregoing as well as other objects of the invention will become more readily apparent by reference to the various figures of the drawing wherein.

Figure 1:
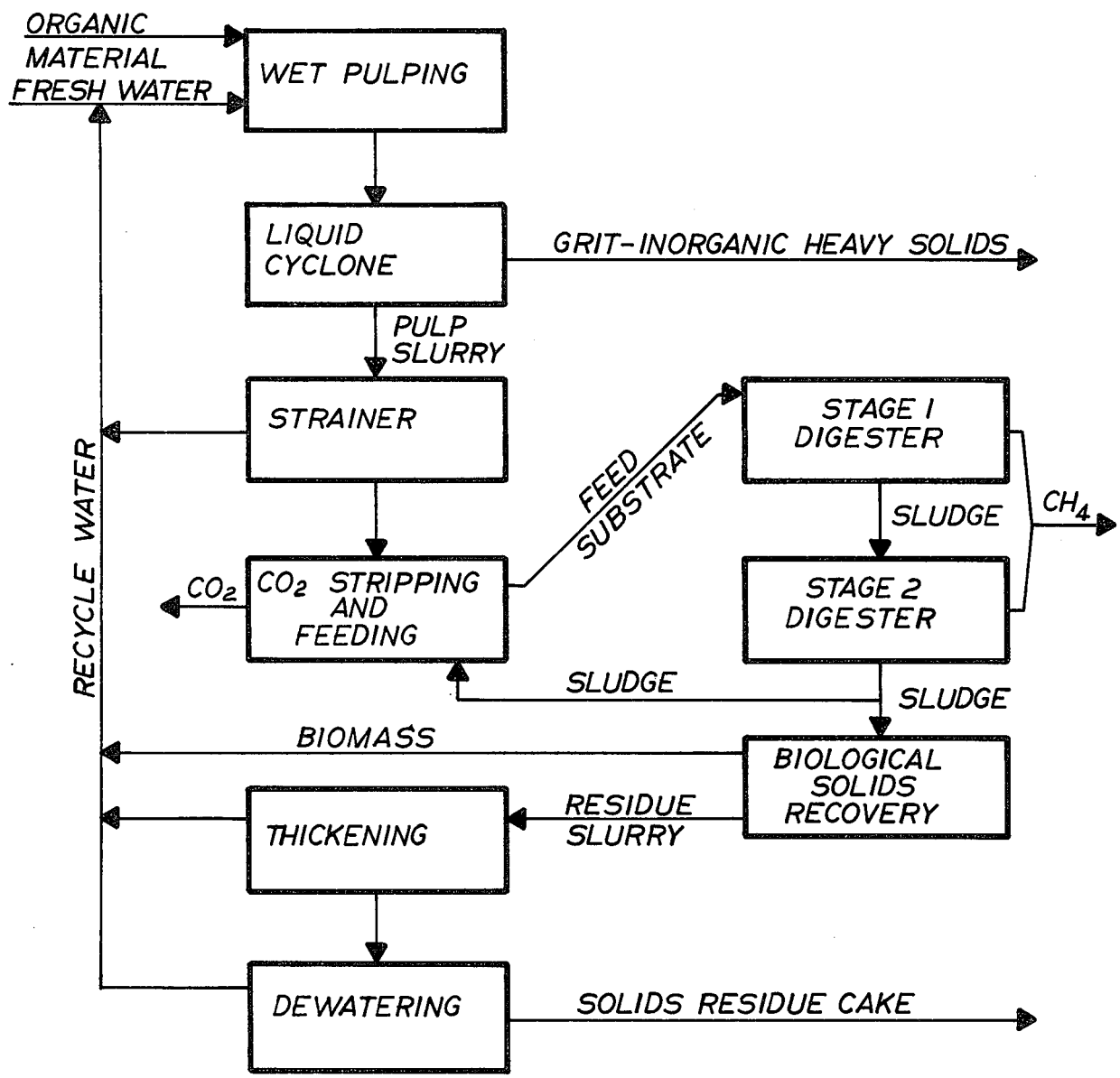
FIG. 1 is a flow sheet of the preferred embodiment of the present invention.

Referring now in greater detail to the various figures of the drawing, it will be seen from FIG. 1 that organic material is slurried or pulped in a wet pulping tank where it is mixed with recycled water and fresh water into a slurry with a minimum of 4% solids by weight. The slurrying or pulping tank is of steel construction and the organic solids and water within, are impacted at high speed with a rotor having a hardened steel surface. The rotor is mounted on a vertical shaft which gives the rotor blades a speed of about 5,000 feet per minute. A perforated bottom plate in the tank, in conjunction with rotating member, produces a rasp and sieve effect. Drive requirement for the rotor is approximately 40 horse power for each ton per hour of organic feed material (drive basis). The unit operates much as a scaled-up home garbage disposal unit. Wet pulpers are commercially available.

The slurry is then passed from the wet pulping tank through a liquid cyclone for removal of grit and inorganic heavy solids. The liquid cyclone is of steel construction and operates on as little as 4 feet of hydraulic head. An optimal operating range is approximately 10% to 15% underflow. Commercial units of the liquid cyclone tank are readily available.

The underflow from the cyclone tank is dewatered and wasted. Overflow from the cyclone tank next passes through a strainer which dewaters the slurry to a minimum solids content of about 10%. The strainer unit is capable of retaining most material which is larger than 0.10 inches in particle size. Commercial strainer units are also readily available.

Excess water from the strainer is recycled to the wet pulping tank. The dewatered slurry is then transmitted to a carbon dioxide stripping and feeding tank which is a progressing cavity pump well that will hereinafter be termed as the feeding tank. The slurry is well blended in the feeding tank with recirculation sludge from the stage 2 digester, which sludge has been acidified, nutrient-balanced and carbon dioxide stripped. In the feeding tank there is a progress-cavity type pump that is capable of pumping thick slurries under a variety of conditions and is commercially available.

The blended material in the feeding tank is then pumped into the stage 1 digester which is constructed of reinforced concrete or steel. The interior of the stage 1 digester is coated with a corrosion-protective material, especially near the upper edges which will be adjacent the intended liquid-gas interface in the tank. Mechanical mixing capability is provided by auger-type mixers so that the contents of the tank will be well mixed. It is intended that there be an auger, propeller or axial flow impeller which will pump a total of approximately 12 times the tank volume in a 24 hour period assuming no hydrostatic head to overcome and a rather nominal dynamic head due to friction. Such an impeller or pump requires approximately a one horse power drive for each 30,000 gallons of tank capacity in the range of tanks of having volumes of 100,000 gallons to 1,000,000 gallons where the tank is either spherical or square cylindrical design (where $D=h$). The tank should also be baffled in ways well known to those skilled in the art, to prevent short circuiting.

Feed into a spherical tank should be tangential at the equator of the tank and discharge from the bottom.

It is preferred that the feed into the stage 1 digester have a carbon-to-nitrogen ratio of 5 to 1 and a carbon-to-phosphorous ratio of 20 to 1. The nutrients may be conveniently supplied as required, by adding ammonia and phosphoric acid to the sulphuric acid which is fed to adjust pH for carbon dioxide stripping. Unadjusted effluent will have a pH of 6.8 to 7.0 which is adjusted downwardly to 6.4 to 6.5. A pH as low as 6.0 may be tolerated. A chemical solution feeder suitable for strong acid handling is used. However, where organic solids such as manure is being fed, then usually the nitrogen addition can be dispensed with or considerably reduced. However, with municipal waste, the nitrogen addition is most desirable.

The sludge from the stage 1 tank is transferred into the stage 2 tank. The stage 2 tank is identical to the stage 1 tank except mixing is continuous in the stage 1 tank, but mixing is intermittent in the stage 2 tank. These are preferable approaches, but if desired mixing can be intermittent or continuous in both tanks. Intermittent mixing is preferable in the stage 2 tank as this will allow the development of a thicker mixture and allow some settling of solids as a preparatory step toward dewatering and thickening of the solids. Continuous mixing is preferred in the stage 1 tank because of the relative freshness of the material in the tank which will promote a greater yield of methane. Intermittent mixing in the stage 2 tank is about five to ten minutes every two hours.

The stage 1 and stage 2 tanks are basically open volumes which hold the slurry from which the methane will be obtained. It is not necessary to provide plates or special elements inside of the tank except for the mixing means, although in some uses baffles or other means may be provided. It is preferred that the stage 1 and stage 2 tanks be spherical as this reduces feed loss and also minimizes construction costs. However, the tanks can be of other shapes, such as cylindrical.

The digestion process in both stage 1 and stage 2 tanks may be operated either mesophilically (approximately 40° C) or thermophilically (approximately 60° C), but thermophilic operation has certain advantages including a lower solids retention time (SRT) and the thermophilic sludge usually dewaters more readily.

It should be kept in mind that solids retention time (SRT) has to do with discharge of sludge from the stage 2 tank to the biological solids recovery. The SRT is a ratio calculated by weight of the sludge being discharged from the stage 2 tank dividing the total weight of the sludge in the stage 1 and stage 2 tanks by the weight of solids discharged from the stage 2 tank during a given time. For example, where the weight of dry solids combined in the stage 1 and stage 2 tanks total 50 tons, and there are 10 tons of dry solids per day being discharged from the stage 2 tank, the resulting SRT is five days.

In carrying out the digesting process at either approximately 40° C or 60° C a small amount of the methane produced by the process is used to heat the liquid input to the tanks or the contents of the tanks in order to maintain the desired temperature.

It has been recognized that the rate of digestion peaks at about 35° C to 40° C (mesophilic) and then drops at slightly higher temperature. However, the rate then climbs to a still higher point at about 55° C to 60° C (thermophilic) and a second, but higher peak is achieved. Thus, operation at about 60° C achieves a higher digestion rate, such that SRT is four to five days in the stage 1 tank and four to five days in the stage 2 tank. This compares favorably with an SRT of 12 to 15 days total for the two tanks when operating at 40° C.

The liquid retention time (LRT) for the two tanks combined should be approximately 48 hours, although as little as 24 hours may suffice and as many as 72 hours may be necessary depending upon the gas quality desired and the volume-to-interface ration (V/I) used. LRT is calculated by determining the total volume of liquid in the stage 1 and stage 2 tanks and dividing by the volume of liquid fed back into the stage 1 tank. Thus, if the total volume of liquid in stage 1 and stage 2 tanks is 200,000 gallons and if a 100,000 gallons of liquid is fed back into the stage 1 tank in a 24 hour period, there is an LRT of 48 hours or 2 days.

With a 48 hour LRT, a gaseous product of approximately 90% methane can be produced at a V/I of approximately 400 (gallons per square foot of interface). As the LRT changes, the quotient of LRT divided by the V/I should remain approximately 0.12. With appropriate changes in LRT, a V/I range of 200 to 500 is most desirable. If the LRT becomes longer, then the appropriate V/I ratio must be greater.

With a 48 hour LRT, a portion of the effluent from the stage 2 tank, equal to the feed volume from the strainer, is separated for dewatering with solids recovery for by-products and water being recycled to the pulping operation. Dewatering may be achieved by several different means, including a centrifuge, vacuum filter or pressure filter. But in the preferred embodiment a two step process is used. This two step process employs a mechanical thickening device called a hydradenser followed by a cone press. The first step increases solids content of the sludge from a nominal 8% to a nominal 15%. The cone press then increases the solids contents to approximately 50%.

The recycling of water conserves energy and enhances process stability by recycling buffering. The recirculated portion of the stage 2 effluent has acid-nutrient solution added to increase availability of carbon dioxide for stripping. Also, this is where adjustments are made so as to have a carbon to nitrogen ratio of 5 to 1 and carbon to phosphorous ratio of 20 to 1 as previously discussed.

A plate-type stripping tower is used to strip the carbon dioxide. The primary considerations in the stripping tower design there are (1) To produce the maximum possible surface area in the sludge to enhance transfer of carbon dioxide across the liquid-gas interface; and (2) To provide adequate airflow to remove the carbon dioxide which has been transferred. Alternatively, a cyclonic spray tower may be used.

The volume-to-interface (V/I) ratio of the digesting substrate in the stage one and stage two tanks is a direct measure of rates of molecular diffusion. The ratio itself is in terms of gallons per square foot of interface which underscores the fact that the diffusion can take place only at the interface between the slurry and the air space above the slurry in the digesting tank. Liquid retention time (LRT), pH and temperature are also factors as already somewhat covered and as will be discussed in more detail.

The coefficient of diffusion for carbon dioxide in a well-stirred system is approximately 7.5 centimeters per hour. The coefficient of diffusion decreases as molecular weight increases. Furthermore, for gases the coefficient of diffusion varies as the square root of the density of the gas. By calculation it can be shown, on the basis of the foregoing, that methane has a coefficient diffusion which is approximately $4\frac{1}{2}$ times (4.53) that of carbon dioxide.

Where molecular diffusion is the means of mass transfer, the area of liquid-gas interface controls the rate of absorption by or desorption by or desorption from the liquid. This is because all transfer between the liquid and gas must take place at the interface. The volume-to-interface (V/I) ratio reflects the rate of molecular diffusion and is a very important consideration in maximizing gas quality from an anaerobic digestion system by maximizing the evolution of methane and minimizing the evolution of carbon dioxide.

The volume-to-interface ratio (V/I) can be varied most readily by changes in operating levels in existing tanks or by variations in tank geometry in new facilities. The following table shows how the V/I ratio changes on a spherical tank for various operating levels:

TABLE 1

Volume-to-interface ratios for spherical tanks at various depths

| % Depth | % Volume | (V/I) Gal/Sq. Ft. |
|---|---|---|
| 100.00 | 100.00 | Infinite |
| 96.67 | 99.67 | 1112.5 |
| 93.33 | 98.65 | 592.3 |
| 90.00 | 97.13 | 405.0 |
| 86.67 | 95.14 | 308.8 |
| 83.33 | 92.59 | 249.3 |
| 80.00 | 89.60 | 210.1 |
| 76.67 | 86.21 | 180.5 |
| 73.33 | 82.46 | 157.4 |
| 70.00 | 78.40 | 139.0 |
| 66.67 | 74.08 | 124.1 |
| 63.33 | 69.53 | 111.7 |

Figure 2:
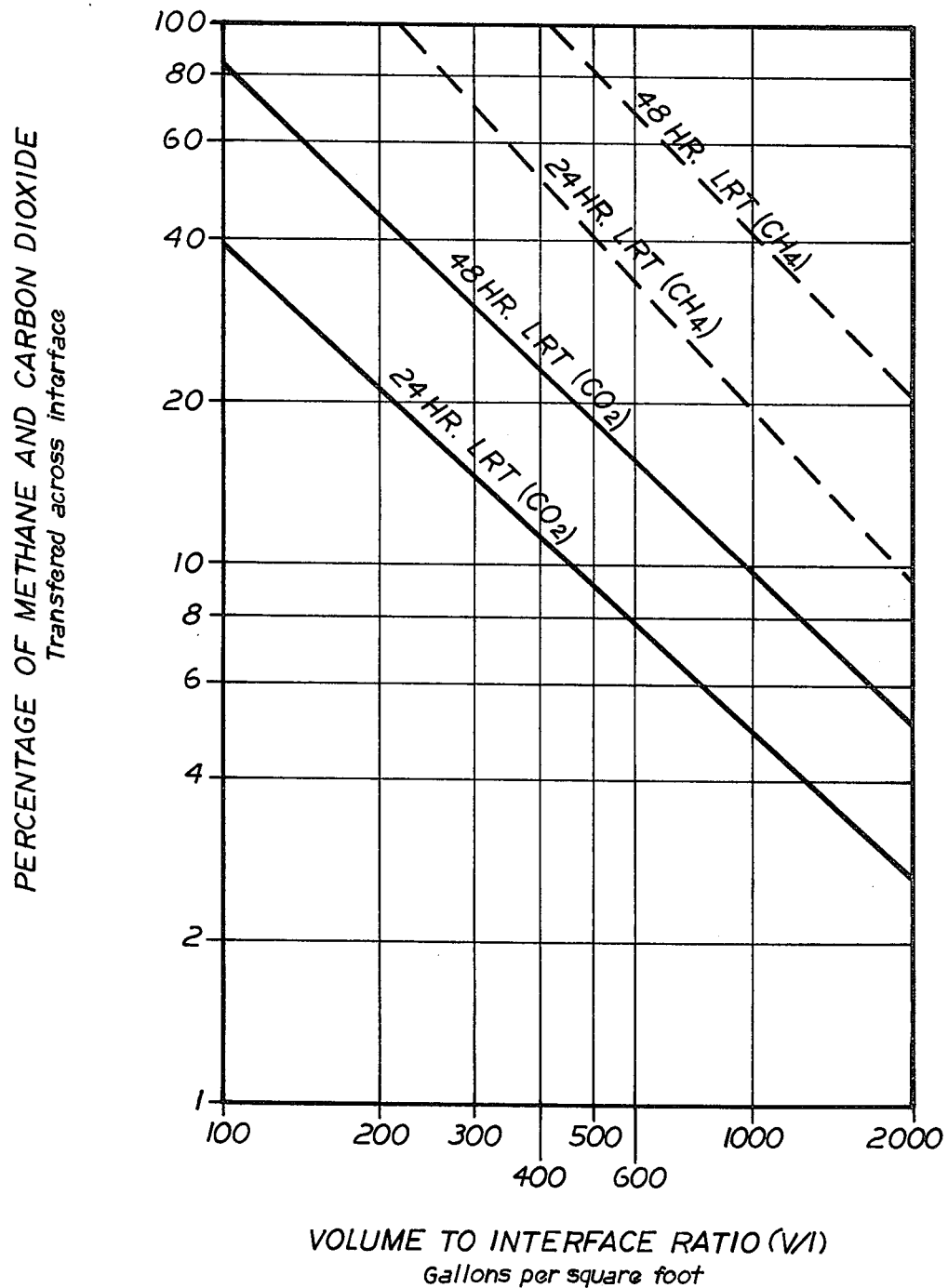
FIG. 2 is a chart showing the effect of volume-to-interface ratio on the transfer of carbon dioxide and methane.

Attention is now called to FIG. 2 which shows the effect of volume-to-interface ratio and liquid retention time (LRT) upon the percentage of methane and carbon dioxide transferred across the interface. FIG. 2 is calculated on the basis of a molecular diffusion rate of 7.5 centimeters per hour for carbon dioxide and a corresponding rate of 4.53 time 7.5 centimeters per hour for the methane. By using the foregoing molecular diffusion rates to calculate transfer volumes for various V/I ratios, FIG. 2 was prepared for both carbon dioxide and methane transfer.

From FIG. 2 it can be seen that at a 24 hour LRT and a V/I ratio of about 220 virtually all methane will be transferred while only 21% of the carbon dioxide will be transferred. At a 48 hour LRT and a V/I ratio of 410, all of the methane and 26% of the carbon dioxide will be transferred. At an LRT of 72 hours and a V/I ratio of 640, all of the methane and about 30% of the carbon dioxide will be transferred. From an economic standpoint the lower LRT values are preferred.

In view of the foregoing, it can be seen that the stage one and stage two tanks should be operated at a 24 hour LRT under conditions that the tank is filled for 80% of its depth which calculates out to a filled volume of 89.6% of the total volume of the tank in accordance with figures taken from Table I. This will give a V/I ratio of 210. From FIG. 2 it can be seen that at a 24 hour LRT and a V/I ratio of 210 virtually all of the methane will be transferred and only about 21% of the carbon dioxide will be transferred.

The most effective operating pH range is from $6\frac{1}{2}$ to 7 or slightly on the acid side.

The sludge discharged from the stage 2 tank is then treated for carbon dioxide stripping.

Returning now to FIG. 2, it can be seen that for a LRT, for example a 24 hour LRT, the percentage of methane transferred across the interface is considerably higher than the percentage of carbon dioxide. This reflects the greater molecular diffusion rate of methane. Through the present invention it has been recognized that LRT can be correlated with the V/I ratio such that with judicious selection there will be 100% recovery of methane and a corresponding small percentage recovery of carbon dioxide. The relationship of Table I showing the V/I ratios, and FIG. 2 showing the relationship between V/I ratio, LRT and percentage of transfer of gaseous methane and carbon dioxide is quite important.

With a 24 hour LRT 100% methane recovery is achieved at a V/I ratio of about 220 which is where the spherical tank of Table I is filled for 80% of its depth. A decision must be made based on economics whether to run the process at a 24 hour LRT, a 48 hour LRT or smaller or greater LRT's.

It should be kept in mind that LRT is the ratio of the combined volumes of tank 1 and tank 2 divided by the volume of liquid fed back to tank 1. Once tank 1 and tank 2 are selected, their combined total volume is a constant and the only variable effecting LRT is the volume of liquid fed back to tank 1. Increasing the volume of liquid fed back to tanks 1 will cause a reduction in LRT such that the process could be operated, for example at a 24 hour LRT instead of a 48 hour LRT by doubling the volume of liquid fed back to tank 1. This would necessitate changing the V/I ratio from 410 to 220 in order to achieve a 100% recovery of methane, but it should be noted that when operating at the 24 hour LRT, rather than the 48 hour LRT, that there is a higher percentage of carbon dioxide in the resulting gas. Hence, the operation at the 48 hour LRT results in a higher percentage of gaseous methane in the resulting gas.

It should be further kept in mind that in considering the operation at a V/I ratio of 220 instead of 410, that this means operating with the tank filled to 80% of its depth rather than 90% of its depth, which amounts to less use of available equipment and hence a somewhat negative economic effect. Of course, the loss incurred by operating at 80% of depth, rather than 90% of depth may be more than compensated by operation at a higher LRT which means the saving of energy because there is only 50% of the volume of liquid fed back to tank 1. The actual choice of operation will depend upon the economics at the time of operation, but in any event, the present invention will be practiced to achieve, in an economical way, a gaseous product which is very high in methane content.

Through the present invention slurry is maintained at a desired V/I ratio and for a desired liquid retention time, such that most, if not all of the methane, is transferred across the interface while a minor amount of the carbon dioxide is transferred across the interface.

The bulk of the carbon dioxide remains in a spent slurry which is transferred as sludge to a loop for carbon dioxide stripping which is greatly improved by adjustment of pH with acid.

Figure 3:
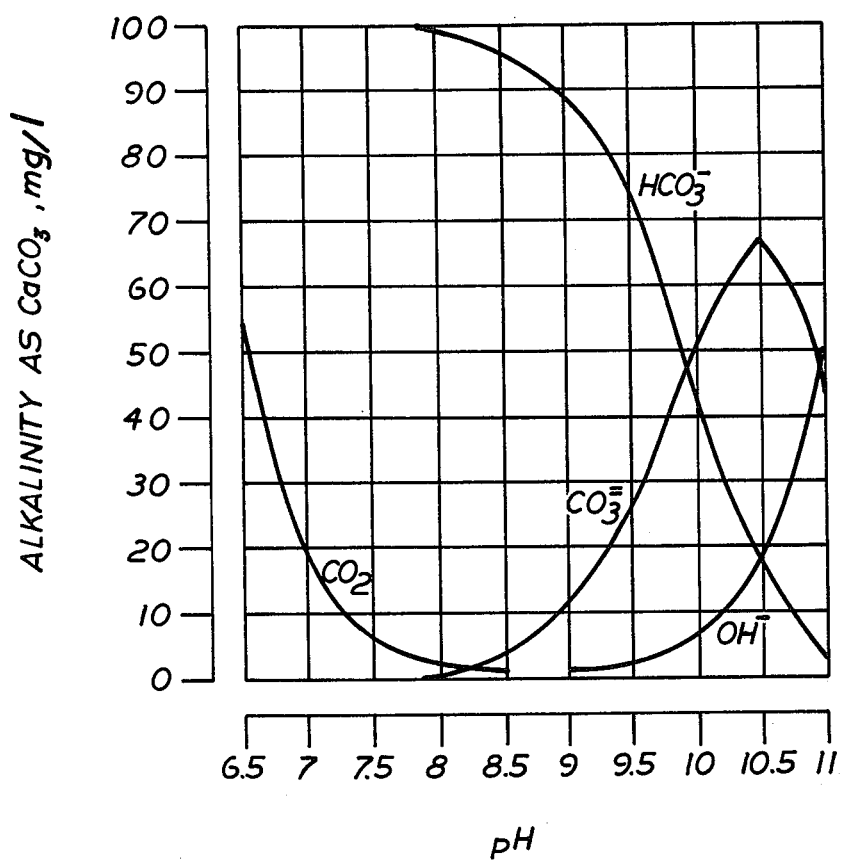
FIG. 3 is a chart showing the alkalinity-carbon dioxide relationships at various pH levels.

It should be kept in mind that carbon dioxide exists in solution in several different forms as indicated in FIG. 3. Carbon dioxide can exist as an equilibrium system between free carbon dioxide and carbonic acid or it exists as bicarbonate or it exists as a carbonate radical. The amounts and proportions of these various forms are dependent upon the pH of the system. FIG. 3 shows how this relationship varies with pH. However, the carbon dioxide is available for transfer outwardly from the liquid side of the interface when the carbon dioxide is in the form of an equilibrium system between free carbon dioxide and carbonic acid. Thus, as indicated in FIG. 3 at pH of 7.0 only 20% of the carbon dioxide in the system is available for transfer which is quite satisfactory when the slurry is in the stage 1 tank or the stage 2 tank when carbon dioxide transfer is undersirable. However, in the stripping and recirculation loop, the pH is adjusted downwardly to 6.5 and the carbon dioxide available for stripping nearly triples as shown in FIG. 3. By recyclying water from the dewatering step, considerable alkaline buffering capacity is recycled. This allows a system to be operated with little or no upward adjustment in pH due to acid input on the stripping loop. The recycled water also offers a sizable savings in energy required to bring new feed material up to operating temperature. Also, the maintenance of the carbon dioxide in a relatively non-available state in the slurry is believed to promote the transfer of gaseous methane out of the liquid or to retard the transfer of the minor amount of carbon dioxide which would otherwise be available for transfer out of the liquid, although the operation of the invention is not necessarily limited to this theory or even dependent upon this theory.

Moreover, the residue from the process of the present invention that is obtained after the final dewatering step, has potential value, either as a soil, organic fertilizer or as a protein-rich animal feed supplement.

In selecting the appropriate V/I ratio and LRT it should be kept in mind that the quotient of LRT divided by the V/I ratio should remain approximately 0.12. Thus, when the V/I ratio is increased from 220 to 410 (approximately doubled) it becomes necessary to double the LRT from 24 to 48 hours. FIG. 2 illustrates the interaction between the V/I ratio and LRT and its effect on yield. It should be kept in mind that evolution of these will take place only at the interface in the tank at the top of the liquid slurry where the air space begins. The faster molecular diffusion rate of methane gas in the well mixed slurry as compared with the carbon dioxide gas, maximizes the evolution of methane and minimizes the evolution of carbon dioxide.

Without further elaboration the foregoing will so fully illustrate my invention that other may, by applying current or future knowledge, readily adapt the same for use under various conditions of service.

What is claimed as the invention is:

1. A process for treating a liquid slurry of organic material to produce a gaseous product comprising a major amount of methane gas and a minor amount of carbon dioxide gas, said process involving anaerobic digestion in a stage 1 digestor and a stage 2 digestor and maintaining said liquid slurry in a well mixed condition under temperature conditions effective in producing said gaseous product, said liquid slurry being maintained in each digester with an air space above defining an interface with said liquid slurry being maintained at a volume-to-interface ratio of at least 100 gal. per ft.$^2$, and a total combined digestor liquid retention time of at least 24 hours whereby the faster molecular diffusion rate of methane gas as compared with carbon dioxide gas enables the passage through said interface of substantial amounts of the methane gas evolving from said slurry while minimizing the passage of carbon dioxide gas through said interface to achieve a gaseous product having a major amount of methane gas and a minor amount of carbon dioxide gas and a spent sludge containing said carbon dioxide, said anaerobic digestion taking place initially by introducing said liquid slurry into a stage 1 digester for a first holding time effective in producing said gaseous product, removing said gaseous product from said stage 1 digester, with the resulting sludge from the stage 1 digester being transferred to a stage 2 digester wherein said anaerobic digestion continues for a second holding time effective in producing said gaseous product, removing said gaseous product from the stage 2 digestor and transferring the spent sludge from the stage 2 digester to a stripping zone wherein the pH of the sludge is adjusted to from 6.0 to 6.5 by the addition of acid, stripping said carbon dioxide from said spend sludge, and recycling said spend sludge from said stripping zone to said stage 1 digester.

2. The process of claim 1 wherein mixing is continuous in the stage 1 digester and intermittent in the stage 2 digester.

3. The process of claim 1 wherein in the volume-to-interface ratio is from 100 to 1,000 gallons per square foot and the quotient of liquid retention time divided by the volume-to-interface ratio is approximately 0.12.

4. The process of claim 1 wherein the volume to interface ratio is from 200 to 500 and the liquid retention time is from approximately 24 to 48 hours.

5. The process of claim 1 wherein the slurry is pulped in a wet pulping digester and mixed with recycled water and fresh water into a slurry with a minimum of 4% solids by weight.

6. The invention of claim 5 wherein the slurry is passed from the wet pulping digester to a liquid cyclone for removal of grit and solids and then through a strainer to dewater the slurry to a minimum content of about 10%.

7. The invention of claim 6 wherein the feed to the stage 1 digester has a carbon-to-nitrogen ratio of 5 to 1 and a carbon-to-phosphorous ratio of 20 to 1.

* * * * *